United States Patent [19]

Shimizu et al.

[11] Patent Number: 5,711,303
[45] Date of Patent: Jan. 27, 1998

[54] DEVICE TO MEASURE VASCULAR FUNCTION

[75] Inventors: Masashi Shimizu, Yokohama; Osamu Shirasaki, Amagasaki; Shinsaku Yanagi, Tokuya-machi; Yoshinori Miyawaki, Otsu, all of Japan

[73] Assignee: Omron Corporation, Kyoto, Japan

[21] Appl. No.: 741,109

[22] Filed: Oct. 30, 1996

Related U.S. Application Data

[62] Division of Ser. No. 245,112, May 17, 1994, Pat. No. 5,582,179.

[30] Foreign Application Priority Data

May 17, 1993 [JP] Japan ..................... 5-114875

[51] Int. Cl.$^6$ ..................... A61B 5/02
[52] U.S. Cl. ..................... 128/687; 128/694
[58] Field of Search ..................... 128/668, 672, 128/677, 680–3, 687–91, 694

[56] References Cited

U.S. PATENT DOCUMENTS

| | | | |
|---|---|---|---|
| 4,524,777 | 6/1985 | Kisioka et al. | 128/677 |
| 5,054,494 | 10/1991 | Lazzaro et al. | 128/677 |
| 5,152,297 | 10/1992 | Meister et al. | 128/672 |
| 5,241,963 | 9/1993 | Shankar | 128/694 |
| 5,316,006 | 5/1994 | Inage et al. | 128/681 |
| 5,368,039 | 11/1994 | Moses | 128/681 |
| 5,385,149 | 1/1995 | Chang et al. | 128/680 |

*Primary Examiner*—Jennifer Bahr
*Assistant Examiner*—Eric F. Winakur
*Attorney, Agent, or Firm*—Morrison & Foerster LLP

[57] ABSTRACT

A measuring device to measure vascular function of an artery includes a cuff that is attachable to a specified part of a body to constrict the artery, a pulse wave amplitude calculating device that calculates an amplitude of a pulse wave that is synchronous with a heartbeat and is based on a change in a volume of the artery, and an inference device that infers a pressure-to-volume characteristic for the artery based on the amplitude of the pulse wave and a corresponding pressure. A blood pressure meter incorporating the measuring device uses a measure of the vascular function to determine a degree of sclerosis in the artery.

19 Claims, 11 Drawing Sheets

DEVICE TO MEASURE VASCULAR FUNCTION

This application is a division of U.S. application Ser. No. 08/245,112 filed May 17, 1994, now U.S. Pat. No. 5,582,179.

BACKGROUND OF THE INVENTION

The invention relates to measuring, in a non-invasive, non-surgical fashion, a vascular function that provides an indication of the expansibility of an artery.

Arteriosclerosis is the most common disease of the circulatory system, and is also the primary cause of a number of other serious illnesses. As arteriosclerosis progresses, qualitative changes and thickening of the material constituting the arterial walls lead to decreased expansibility (the rate of change of the volume, or cross-sectional area, of the arterial lumen with respect to an increase or decrease in internal pressure) of the arteries with respect to internal pressure (i.e., blood pressure).

When arteriosclerosis is advanced, various characteristic symptoms can be observed. Based on these symptoms, a number of methods to estimate the degree of the sclerosis have been devised. These methods include measuring the speed at which pulse waves propagate through the artery, measuring the acceleration of such pulse waves, and monitoring a spectrum of so-called Korotkov sounds. All of these methods involve the detection of changes in particular properties of a signal, where those changes correspond to changes in the dynamic characteristics, such as expansibility, of an artery.

Expansibility of arteries has been measured in animals through experiments in which the internal volume of an extracted artery is measured while the pressure within the artery is gradually increased or decreased, and has also been measured in humans through similar experiments performed subsequent to autopsies. For example, FIG. 1 shows the pressure-to-volume curve for the femoral artery of a dog over a range of negative and positive pressures. As shown in FIG. 1, sufficient negative pressure causes the artery to buckle, and thereby close completely, while increasing positive pressure eventually causes the artery to become fully expanded so that increasing pressure causes minimal increases in volume.

Because the shape of the pressure-to-volume curve changes as arteriosclerosis progresses, production of such a curve in a clinical setting would offer a significant diagnostic tool. Though direct measurement of the cross-sectional area (or volume) of an artery in vivo is difficult, indirect methods, such as ultrasound imaging or angiography, have been used. However, in a live subject, the blood pressure within an artery is readily variable over only a limited range (i.e., between the systolic and diastolic pressure). Thus, the full pressure-to-volume curve cannot be produced directly for a living subject.

SUMMARY OF THE INVENTION

In one aspect, generally, the invention features a measuring device to measure vascular function, such as pressure-to-volume characteristics underlying a pressure-to-volume curve, of an artery. The device includes a cuff that is attachable to the person for whom vascular function is being measured, a pulse wave amplitude calculating device that calculates an amplitude of a pulse wave that is synchronous with a heartbeat and is based on a change in a volume of the artery and an inference device that infers a pressure-to-volume characteristic for the artery based on the amplitude of the pulse wave and a corresponding pressure.

The inference device can include a processor that selects a first pulse wave and a second pulse wave that has a corresponding cuff pressure that is separated from a cuff pressure corresponding to the first pulse wave by an amount equal to the difference between a systolic and diastolic blood pressure of a person for whom the vascular function is being measured. The processor then approximates, for cuff pressures in the region between the cuff pressures corresponding to the first and second pulse waves, a function, that can be an exponential function of pressure, that corresponds to the relationship between the arterial pressure and the internal volume of the artery.

After approximating the function, the processor uses the approximated function to determine, for cuff pressures in the region between the cuff pressure corresponding to the second pulse wave and a cuff pressure corresponding to the second pulse wave plus the difference between a systolic and diastolic blood pressure of a person for whom the vascular function is being measured, the relationship between the arterial pressure and the internal volume of the artery.

Next, for cuff pressures greater than the cuff pressure corresponding to the second pulse wave plus the difference between the systolic and diastolic blood pressure of the person for whom the vascular function is being measured, the processor interpolates previously determined data about the relationship between the arterial pressure and the internal volume of the artery to determine the relationship between the arterial pressure and the internal volume of the artery.

The pulse wave amplitude calculating device of the invention can include a pulse wave extracting device that detects and extracts a pulse wave component that is synchronous with a heartbeat and is based on a change in a volume of an artery, and an amplitude calculating device that calculates an amplitude of the pulse wave. Typically, the pulse wave amplitude calculating device calculates the amplitude of multiple pulse waves as a pressure in the cuff changes.

In another aspect, generally, the invention features a blood pressure meter that judges the degree of sclerosis in an artery. The blood pressure meter includes a cuff that is attachable to a specified part of the body to constrict an artery, a pulse wave extracting device to detect and extract a pulse wave component that is synchronous with a heartbeat based on a change in a volume of the artery when a cuff pressure in the cuff changes, an amplitude calculating device to calculate an amplitude of the pulse wave, a blood pressure calculating device to calculate a systolic blood pressure and diastolic blood pressure based on the cuff pressure and the amplitude of the pulse wave, an inference device that infers a pressure-to-volume characteristic of the artery based on the amplitude of the pulse wave and the corresponding cuff pressure, and a judging device that determines a degree of sclerosis in the artery based on the pressure-to-volume characteristic. Typically, the judging device judges the degree of sclerosis by comparing the pressure-to-volume characteristic to a predetermined pressure-to-volume characteristic. The blood pressure meter can include an input device to input an age of the person for whom arteriosclerosis is being detected, in which case the judging device uses the age to select the predetermined pressure-to-volume characteristic. The blood pressure meter can also include a display that displays the results produced by the judging device.

DESCRIPTION OF THE PREFERRED EMBODIMENTS

Changes in arterial volume when the artery is pressurized by a cuff can be measured by monitoring vibrations, or pulse waves, produced by blood pressure changes in the artery. When the pressure inside the artery differs from that outside the artery, the internal pressure in the artery (i.e., the blood pressure) will oscillate between systolic and diastolic pressure. The artery, which is a sort of elastic tube, experiences repeated changes in volume as it expands and contracts in response to the oscillating blood pressure, and these changes in volume affect the amplitude of the pulse waves produced within the artery. Approaches to measuring the amplitude of the pulse waves include measuring the electrical impedance of a limb to which the cuff is attached, photoelectrically measuring the quantity of light reflected by the limb, or monitoring, through the cuff, variations in the internal pressure in the arteries of the limb.

Figure 2A:
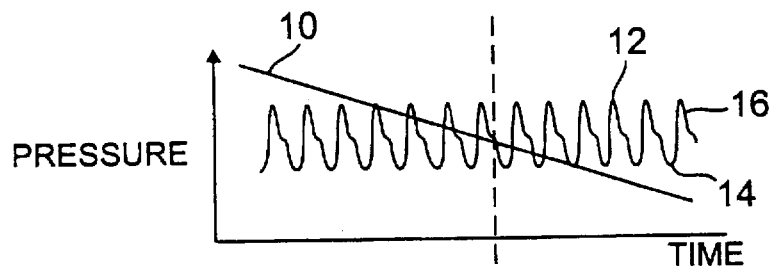
FIGS. 2A and 2B are graphs of the relationship between cuff pressure (external pressure), internal arterial pressure, and pulse wave amplitude.
Figure 2B:
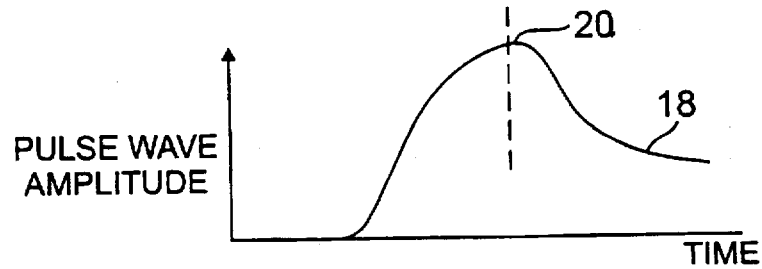

As illustrated in FIGS. 2A and 2B, if the cuff pressure 10 is varied over a range that includes the systolic pressure 12 and the diastolic pressure 14 of the artery's internal pressure 16, and the pulse wave amplitude 18 is observed and recorded, the resulting graph of the pulse wave amplitude will have a maximum value 20 near a cuff pressure that equals the average blood pressure.

Figure 3:
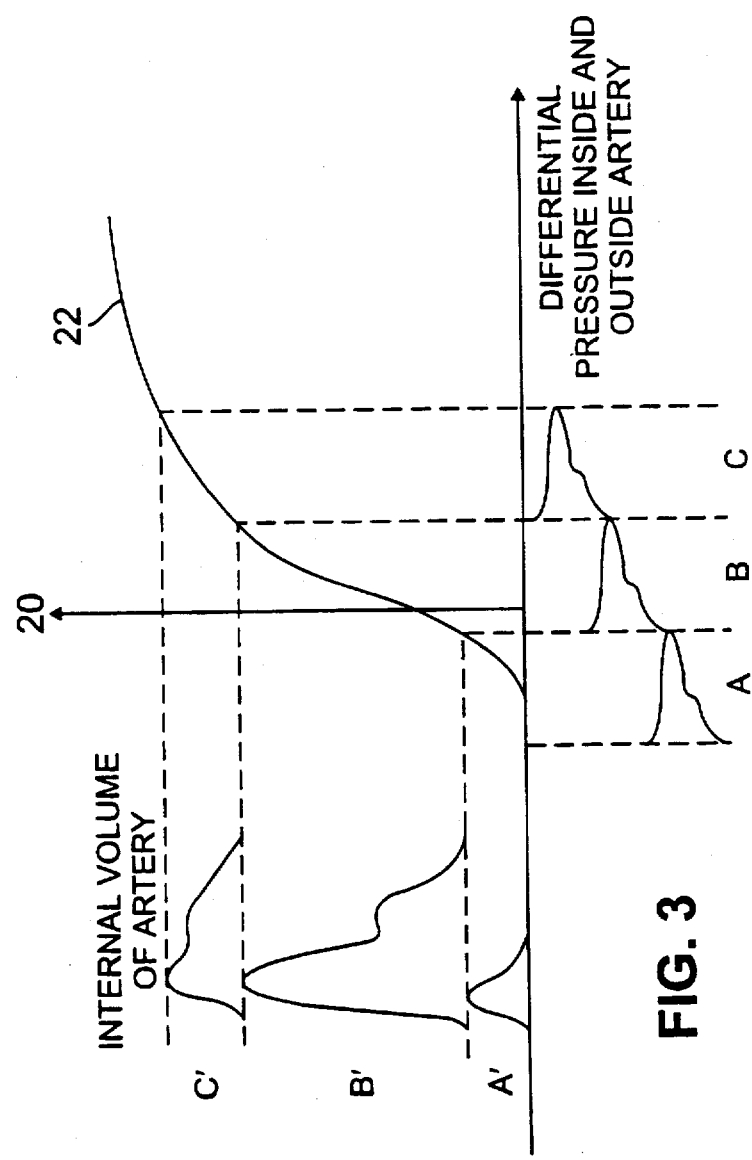
FIGS. 3-4 are graphs of the relationship between differential pressure in an artery and the volume of the artery.

As illustrated in FIG. 3, the internal volume of the artery, as well as the rate of change (expansibility) in the internal volume of the artery, varies with the differential pressure between the inside of the artery and the outside of the artery (internal blood pressure 12 minus cuff pressure 10). At sufficiently negative differential pressures, the artery is buckled and the slope of the pressure-to-volume ("PV") curve 22 is zero. At these pressures, a pressure pulse caused by a heartbeat has no effect on the volume of the artery. As the differential pressure becomes less negative, the artery begins to unbuckle, and a heartbeat begins to affect the volume of the artery. For example, because the artery is unbuckled during only a portion of heartbeat A, artery volume is only changed as illustrated by A'. Increasing differential pressure causes heartbeats to have increasing affect on the volume of the artery until the differential pressure reaches zero, which corresponds to the point 20 at which the pulse wave amplitude 18 has its maximum value. At this point, which is illustrated by heartbeat B and volume change B', the artery is in a so-called high compliance mode, and a change in volume relative to a change in internal-to-external differential pressure is at its maximum. As the differential pressure continues to increase, the arterial walls gradually approach their fully distended state, and the change in volume caused by a heartbeat begins to decrease. For example, heartbeat C causes a much smaller volume change (C') than the volume change (B') caused by heartbeat B.

When an artery having the PV curve 22 discussed above is subjected to a periodically oscillating internal pressure and a steadily increasing (or decreasing) external pressure, it will exhibit the change in pulse wave amplitude shown in FIG. 2B. Thus, because the differential pressure can be varied beyond the range indicated by the difference between the systolic and diastolic pressures, the PV curve 22 can be produced for a wide range of pressures by varying the cuff pressure and measuring the pulse wave amplitude.

A measure of the behavior of the pulse wave amplitude in response to pressure is obtained using the well known oscillometric technique for measuring blood pressure. As described below, the invention then generates the PV curve 22 from the change in pulse wave amplitude (hereafter, the pulse wave envelope) in response to pressure. (Though, for ease of description, reference is made to generating the PV curve, it will be appreciated that the physical curve need not be generated. Rather, the data corresponding to the curve is what is truly of significance.

Figure 4:
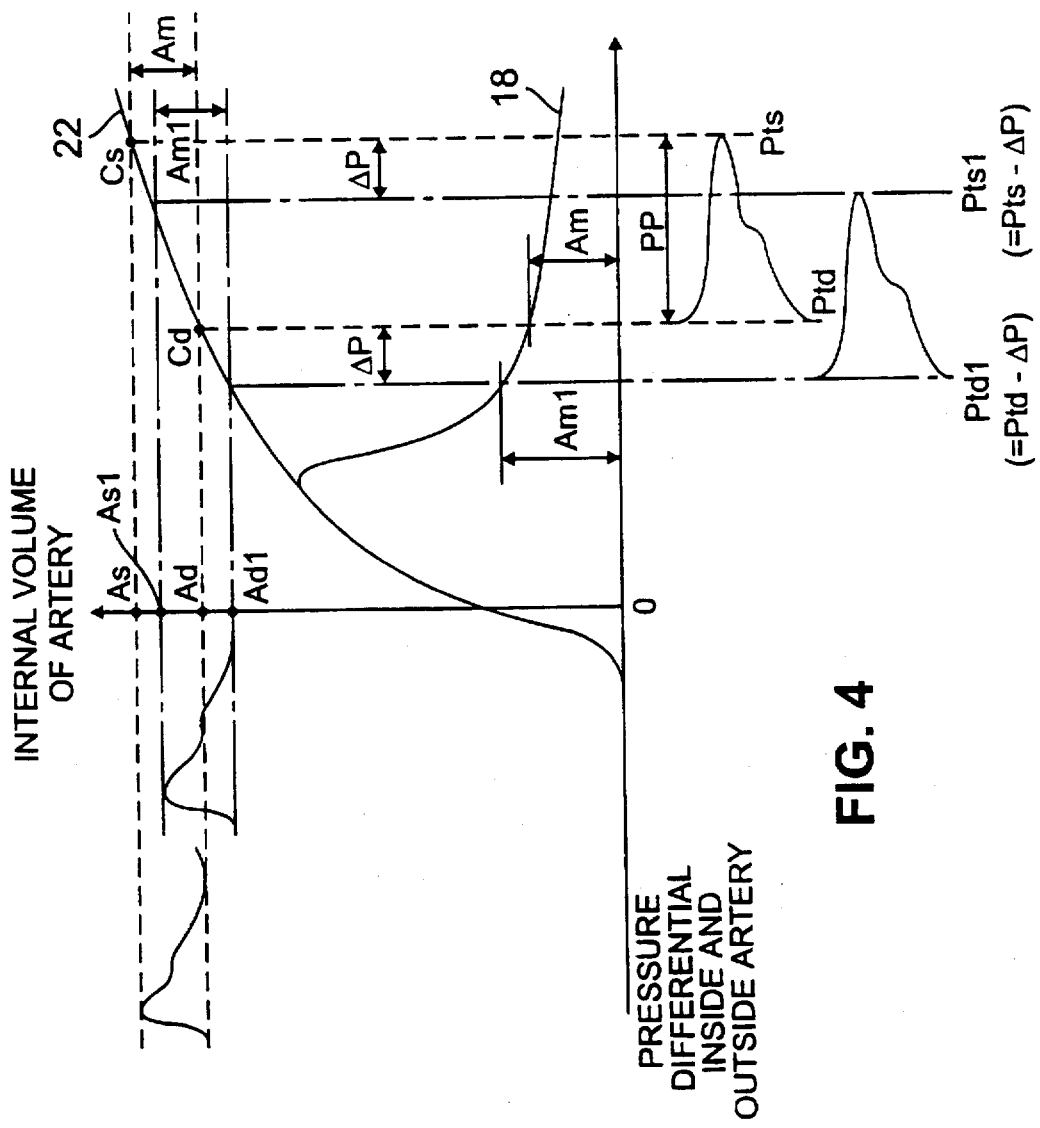

Referring to FIG. 4, a pulse wave with amplitude $A_m$ at a given cuff pressure can be explained as follows. The internal-to-external differential pressure $P_t$, which accompanies changes in blood pressure moves from value $P_{td}$ at the point of diastolic pressure to value $P_{ts}$ at the systolic pressure, which corresponds to a movement along PV curve 22 from point $C_d$ to $C_s$, and a change in the volume (which corresponds to the pulse wave amplitude) from $A_d$ to $A_s$. In other words, the difference, $A_m$, between the volume of the artery, $A_d$, at a given diastolic pressure, $P_{td}$, and the volume of the artery, $A_s$, when the differential pressure has been increased by one pulse pressure, PP (the difference between systolic and diastolic pressure), can be expressed as the amplitude of the pulse wave. Thus, the volume A, at point $C_s$ can be expressed as:

$$A_s = A_d + A_m \quad (1)$$

If the pulse wave is then expressed at another pressure, so that the differential pressure, $P_{tdl}$ ($P_{td}-\Delta P$), corresponding to the diastolic pressure is $\Delta P$ less than $P_{td}$, a pulse wave, $A_{ml}$, can be observed as the curve changes from differential pressure $P_{tdl}$ to systolic pressure point $P_{tsl}$. Assuming that the PV curve 22 between points $C_d$ and $C_s$ can be expressed as a function, F($P_t$), of the differential pressure $P_t$, then the value $A_{sl}$ of the PV curve 22 at $P_{tsl}$ equals F($P_{ts}-\Delta P$). Because the observed pulse wave amplitude is $A_{ml}$, the value $A_{dl}$ of the PV curve 22 at the diastolic pressure point $P_{tdl}$, (i.e., the value resulting when amplitude $A_{ml}$ is subtracted from $A_{sl}$), is $$A_{dl} = F(P_{ts}-\Delta P) - A_{ml} \quad (2)$$

By repeatedly performing this operation with differing values of $\Delta P$, the PV curve 22 can be obtained for the range of differential pressures for which the systolic pressure ($P_{ts}-\Delta P$) equals or exceeds $P_{td}$, the first diastolic pressure point. For the remaining differential pressures, the PV curve 22 can be obtained using the PV curve 22 generated for the larger differential pressures.

Figure 1:
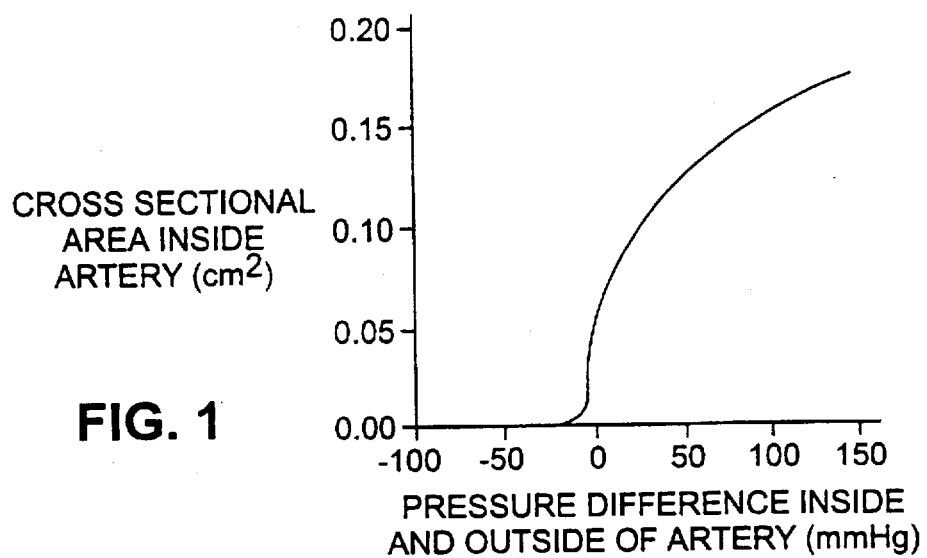
FIG. 1 is a pressure-to-volume curve for the femoral artery of a dog.

Function F($P_t$), which approximates the PV curve 22 between points $C_d$ and $C_s$, is generated as described below. As illustrated in FIG. 1, this function approaches a straight line in the region where the pressure is sufficiently high. For this reason, function $F(P_r)$ could be treated as a straight line. However, to obtain a more precise result, the approach described below is used.

As discussed above, the observed pulse wave amplitude is the difference between the values of the PV curve 22 that are obtained when the pressure is shifted by an amount equal to pulse pressure PP. This relationship can be expressed according to the following formulae. First, based on equation 1:

$$A_m = A_s - A_d \tag{3}$$

Because $A_s$ can be expressed as the pulse wave amplitude when the pressure has been shifted from the pressure yielding $A_d$ by an amount equivalent to the pulse pressure PP, $A_s$ can be expressed as a function of $P_r$ as follows:

$$A_s(P_r) = A_d(P_r + PP) \tag{4}$$

Substituting equation 3 into equation 4 yields:

$$A_m(P_r) = A_d(P_r + PP) - A_d(P_r) \tag{5}$$

where $A_m(P_r)$ is the change in pulse wave amplitude that is actually observable for every value $P_r$. By defining an approximation function $G(P_r)$ for the PV curve, $A_m(P_r)$ can be expressed using an equation dependent on the function $G(P_r)$:

$$A_m(P_r) = G(P_r + PP) - G(P_r) \tag{6}$$

Accordingly, by deciding on the basic form of $G(P_r)$, and approximating equation 6 to the pulse wave envelope, $G(P_r)$ will approximate the PV curve.

The approximation interval can be between any given points $P_{st}$ and $P_{ts}$ ($P_{st} + PP$) with which processing is begun. Using this approximation interval, $G(P_r)$ can be determined by fitting $G(P_r)$ to the pulse wave amplitudes in the interval using, for example, the least squares method. This $G(P_r)$ is then used to generate the PV curve for pulses for which the systolic pressure is greater than $P_{st}$. Thereafter, interpolation techniques are used to generate the remaining portion of the curve.

Figure 5:
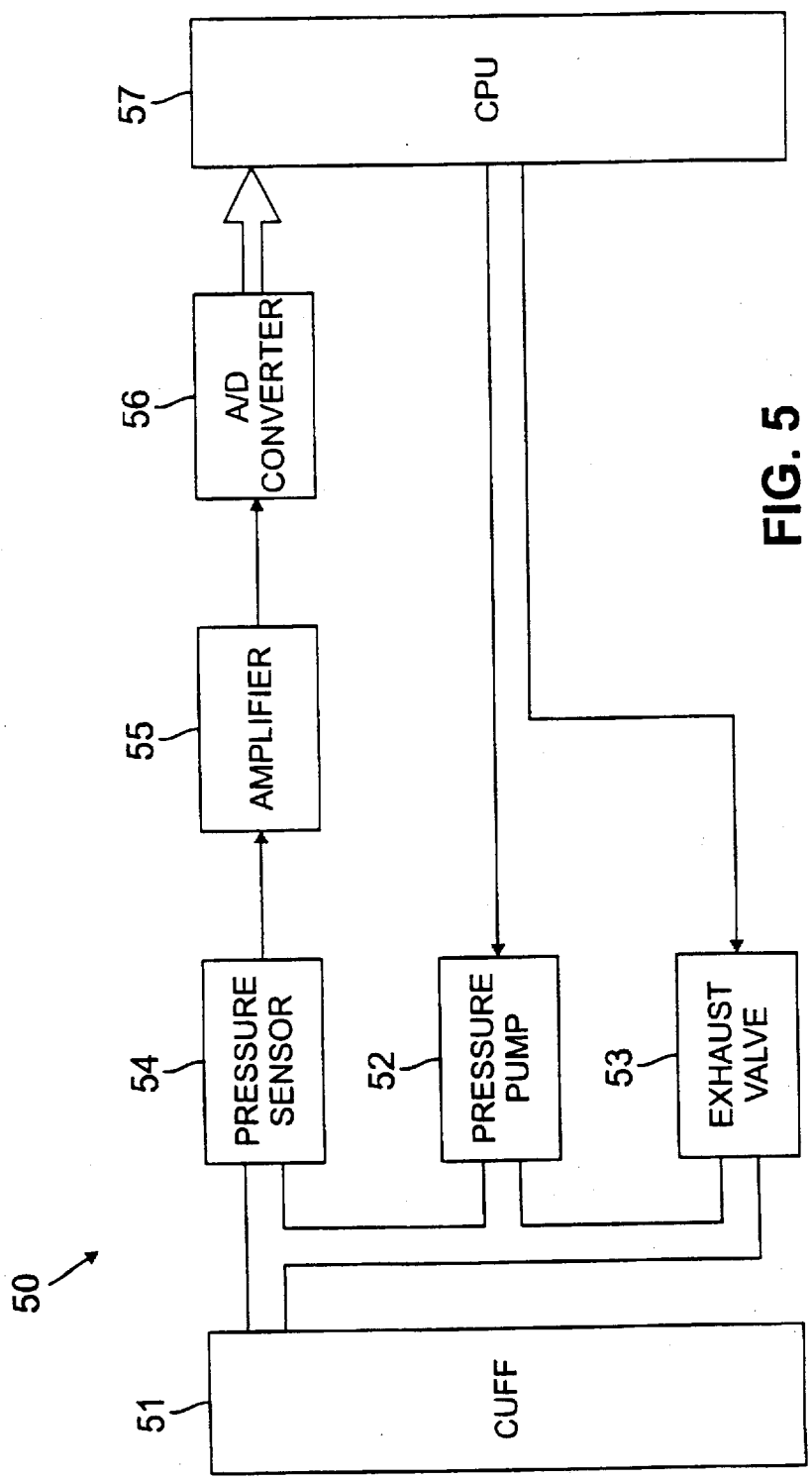
FIG. 5 is a block diagram of a device for measuring vascular function.

Referring to FIG. 5, a device 50 for measuring a vascular function corresponding to PV curve 22 includes a cuff 51 that is attachable to a limb. A pressure pump 52 for increasing cuff pressure, an exhaust valve 53 for decreasing cuff pressure, and a pressure sensor 54 for sensing the amplitude of the pulse wave are connected to cuff 51. An amplifier 55 amplifies signals from pressure sensor 54, and supplies the amplified signals to an A/D converter 56 that converts the signals to digital signals and supplies the digital signals to a central processing unit (CPU) 57. CPU 57 uses the digital signals in determining the PV curve 22 of the limb to which cuff 51 is attached. CPU 57 also controls pressure pump 52 and exhaust valve 53, and thereby controls the pressure in cuff 51.

Like an oscillometric blood pressure meter, device 50 uses as input the pulse waves captured during the process of gradual pressurization (or depressurization) of the cuff, and, for each pulse wave, the cuff pressure when the pulse wave occurs. For this reason, the structure of device 50, to some extent, resembles that of an oscillometric blood pressure meter.

Though internal cuff pressure is used to sense the pulse wave, other approaches, such as electrically measuring the impedance of the limb, or photoelectrically measuring a quantity of light reflected by the limb, could also be used. If one of these approaches were used, pressure sensor 54 would be replaced by an impedance sensor, or a photoelectric sensor, that would then be connected to amplifier 55.

Figure 6:
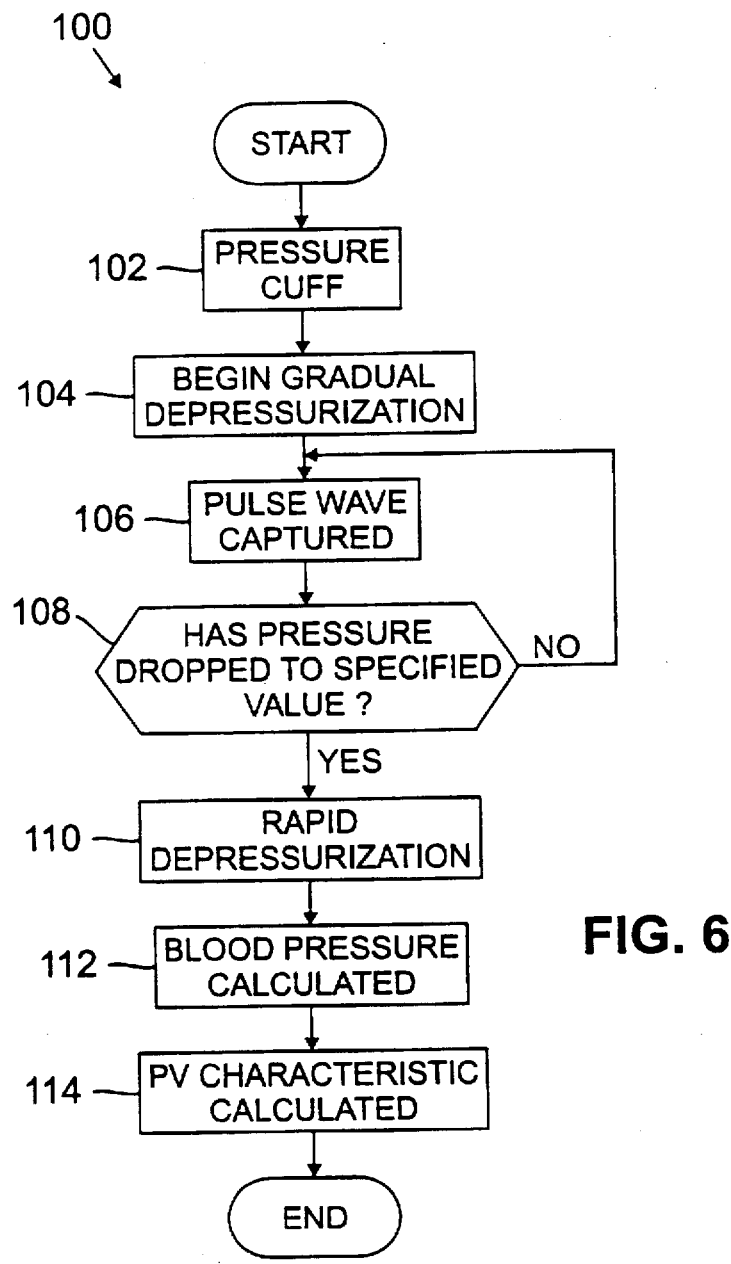
FIGS. 6-8 are flow charts of procedures implemented by the device of FIG. 5.

Referring to FIG. 6, CPU 57 operates device 50 according to a procedure 100. The operations performed by device 50 can be divided broadly into two categories: measurement of blood pressure and generation of the PV curve 22. The blood pressure must be measured in order to obtain the systolic pressure, the diastolic pressure, and the pulse pressure, PP, that is the difference between them. If these values could be obtained by some separate means, device 50 would not need to measure blood pressure. The generation of the PV curve 22 is largely performed after the blood pressure measurement has been completed.

CPU 57 first activates pressure pump 52 to pressurize cuff 51 to a predetermined value (step 102). The predetermined value is set at a pressure 50 mmHg higher than the expected systolic pressure so that the PV curve is generated in a range starting from a differential pressure of approximately negative 50 mmHg. When cuff 51 is completely pressurized, CPU 57 shuts off pressure pump 52 and activates exhaust valve 53 so that air is gradually released from cuff 51 (step 104). As cuff 51 is depressurized, the amplitudes of pulse waves are captured (step 106). In this process, a pulse wave is recognized for each heartbeat and the amplitude of the pulse's oscillation is determined by subtracting out the static portion of the signal provided by A/D converter 56 (which corresponds to the cuff pressure applied to the limb) so that only the dynamic portion, which corresponds to the pulse wave, remains. The value of the cuff pressure at the same moment is detected and is stored in a specified storage area with the pulse wave amplitude. Capture of pulse wave amplitudes is repeated until the cuff pressure falls to a specified value (step 108). Once the cuff pressure falls to the specified value, CPU 57 completely opens exhaust valve 53 to rapidly reduce air pressure remaining in cuff 51 (step 110). Though the measurement of blood pressure and the capture of pulse wave amplitudes occur while the cuff is being gradually depressurized, they could also be performed while the cuff was being gradually pressurized. In addition, cuff 51 could be pressurized or depressurized in steady or stepwise manners.

CPU 57 uses the pulse wave amplitudes captured during gradual depressurization, and their corresponding cuff pressures, to determine the systolic and diastolic blood pressures (step 112). CPU 57 determines these blood pressures using well known oscillometric techniques.

Figure 7:
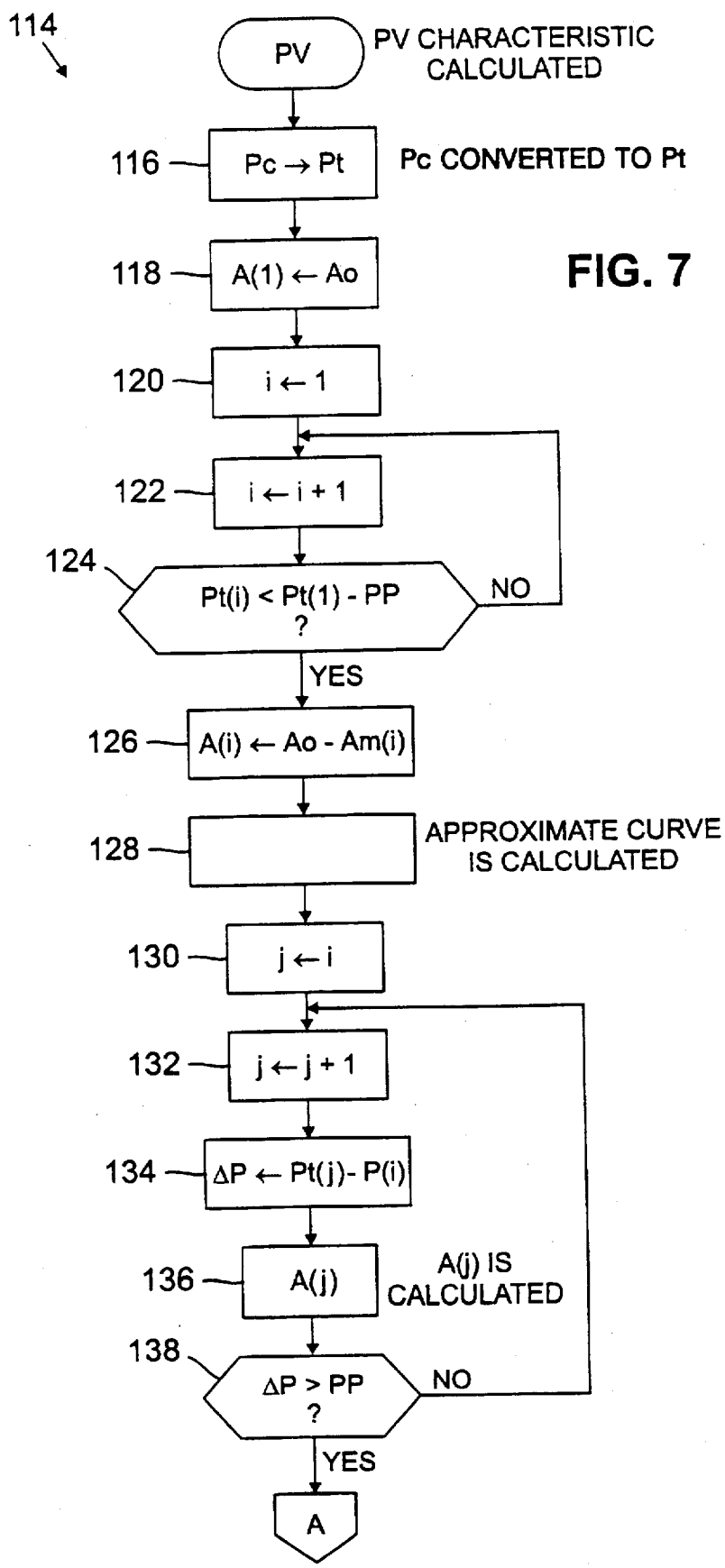
Figure 8:
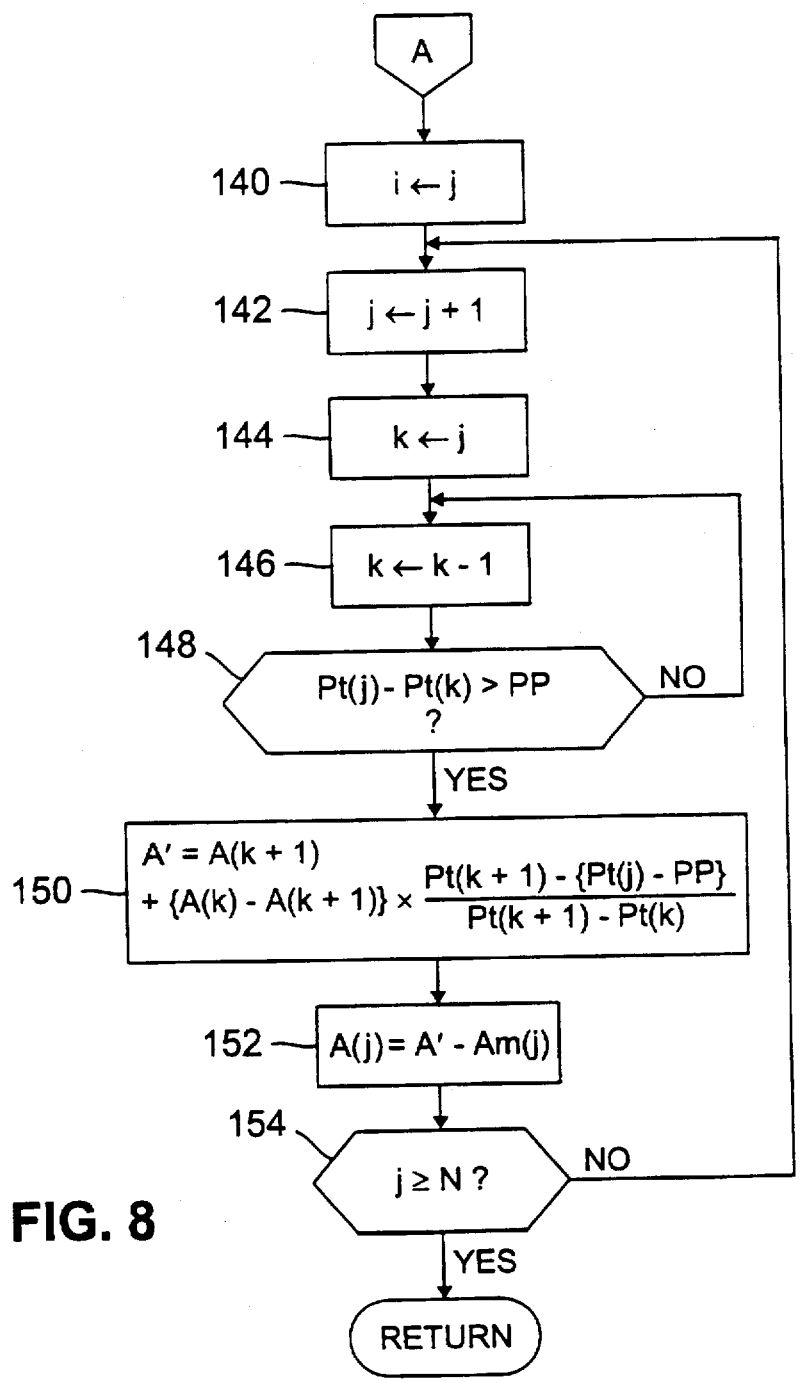

Finally, CPU 57 uses the pulse wave amplitudes, their corresponding cuff pressures, and the systolic and diastolic blood pressures to determine the PV curve of the artery (step 114). The procedure used by CPU 57 to determine the PV curve is illustrated in FIGS. 7–8.

In the following discussion, a particular sample of the pulse wave amplitude is designated $A_m(n)$ and its corresponding cuff pressure is designated $P_c(n)$, where n is the sequence number of the sample, and the last pulse wave to be captured (that is, the one with the lowest cuff pressure) has a sequence number of 1. The systolic and diastolic pressures obtained through measuring the blood pressure are designated, respectively, $P_s$ and $P_d$, and the pulse pressure ($P_s-P_d$) is designated PP. A point on the PV curve is designated as $A(n)$.

To generate the PV curve, CPU 57 first converts the cuff pressures $P_c(i)$ to differential pressures $P_r(i)$ by subtracting the diastolic pressure (step 116). Thus, cuff pressure is converted to differential pressure as follows:

$$P_r(i) = P_c(i) - P_d \tag{7}$$

Next, to obtain an initial value on the PV curve from which subsequent processing will be performed, CPU 57 stores an initial value $A_0$ in the PV curve at the point, A(1), having the lowest differential pressure $P_r(1)$ (step 118).

CPU 57 then finds a differential pressure $P_r(i)$ that is one pulse pressure lower than the maximum differential pressure $P_r(1)$ (steps 120–124). CPU 57 does so by initializing i to 1 (step 120), and incrementing i (step 122) until $P_r(i)$ is less than $P_r(1)$ minus PP ($P_r(i)<P_r(1)-PP$) (step 124). After finding the desired differential pulse value, CPU 57 sets the value A(i) on the PV curve equal to the difference between the pulse wave amplitude $A_m(i)$ at that point and the initial value $A_0$ (step 126):

$$A(i)=A_0-A_m(i) \qquad (8)$$

Next, CPU 57 generates a function that approximates the PV curve (step 128). For example, assuming that the PV curve can be approximated by a quadratic curve:

$$G(P_r(x))=\alpha \cdot P_r(x)^2+\beta \cdot P_r(x)+\gamma \qquad (9)$$

then equation 6 can be rewritten as:

$$A_m(P_r(x)) = [\alpha \cdot P_r(x)^2 + \beta \cdot P_r(x)] - \qquad (10)$$
$$[\alpha \cdot (P_r(x)-PP)^2 + \beta \cdot (P_r(x)-PP)]$$

Values for $\alpha$ and $\beta$ can then be determined by substituting into equation 10 the differential pressures, and the actual values, $A_m(P_r(x))$, of the pulse wave amplitudes at every point between n=1 and n=i, and using the sum of the squares of the differences method:

$$\sum_{n=1}^{i} [A_m(P_r(x)) - Y(P_r(x))]^2 = 0 \qquad (11)$$

where $Y(P_r(x))$ equals $[\alpha \cdot P_r(x)^2+\beta \cdot P_r(x)]-[\alpha \cdot (P_r(x)-PP)^2+\beta \cdot (P_r(x)-PP)]$. After determining $\alpha$ and $\beta$, $\gamma$ is determined by assuming that the initial value $A_0$ is the value corresponding to $P_r(1)$, and substituting $P_r(1)$ for $A_0$ in equation 9 to produce:

$$A_0=\alpha \cdot P_r(1)^2+\beta \cdot P_r(1)+\gamma \qquad (12)$$

$$\therefore \gamma = A_0-\alpha \cdot P_r(1)^2-\beta \cdot P_r(1) \qquad (13)$$

Having determined $\alpha$, $\beta$, and $\gamma$, the approximation formula $G(P_r(x))$ is used to generate the segment of the PV curve for which the pulse wave number n ranges from 1 through i.

CPU 57 then generates the PV curve for pressures less than $P_r(i)$. First, CPU 57 sets the pulse wave counter j equal to i (step 130), where i is the number of the pulse wave that serves as the starting point for processing, and j is the number of the pulse wave that is being processed. CPU 57 then increments j by 1 (step 132) and determines the pressure difference $\Delta P$ between $P_r(j)$, the current differential pressure, and $P_r(i)$, the starting differential pressure ($\Delta P=P_r(j)-P_r(i)$) (step 134).

CPU 57 then determines the value A(j) on the PV curve (step 136):

$$A(j)=G(P_r(j)+\Delta P)-A_m(j) \qquad (14)$$

This procedure (steps 132–136) is repeated until $\Delta P$ is greater than PP (step 138). At that point, the first term in the approximation function, $G(P_r(j)+\Delta P)$, is undefined.

In subsequent processing, CPU 57 uses the value A(x) instead of the undefined function G, so that:

$$A(j)=A(P_r(j)+\Delta P)-A_m(j) \qquad (15)$$

However, since the value A(x) can only be determined discretely for each pulse wave, it is obtained for the intervening times by means of straight line interpolation. Thus, with an interpolation value designated as A', A(j) is determined as:

$$A(j)=A'-A_m(j) \qquad (16)$$

To determine A(j), CPU 57 first sets i equal to j so that i equals the pulse wave number at the start of this portion of processing (step 140). CPU 57 then increments j so that j corresponds to the sample for which A(j) is to be determined (step 142).

Next, CPU 57 retrieves the value of the PV curve for the pressure point that is exactly one PP lower than the differential pressure $P_r(j)$ that corresponds to the pulse wave that is being processed. CPU 57 does so by initializing a variable k to equal j (step 144) and decrementing k (step 146) until the distance between the differential pressures $P_r(j)$ and $P_r(k)$ exceeds PP (step 148).

Figure 9:
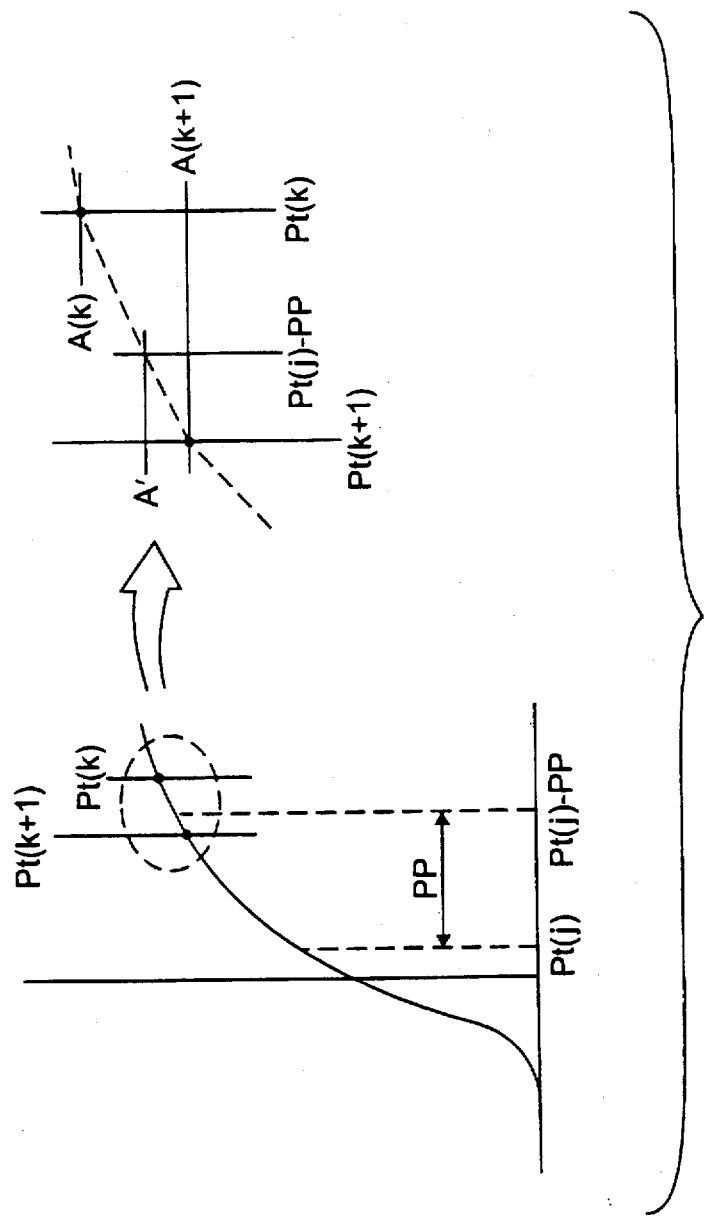
FIG. 9 is a combined graph illustrating straight-line interpolation.

Once the distance exceeds PP, CPU 57 uses straight line interpolation, as graphically illustrated in FIG. 9, to determine A' (step 150):

$$A' = A(k+1) + [A(k) - A(k+1)] \times \frac{P_r(k+1) - [P_r(j)-PP]}{P_r(k+1) - P_r(k)} \qquad (17)$$

CPU 57 then generates the value A(j) on the PV curve as the difference between interpolation value A' and pulse wave amplitude $A_m(j)$.

CPU 57 repeats this process (steps 142–152) until the number j of the pulse wave being processed is equal to the number N of the first pulse wave to be captured. At this point all processing is complete.

Figure 10:
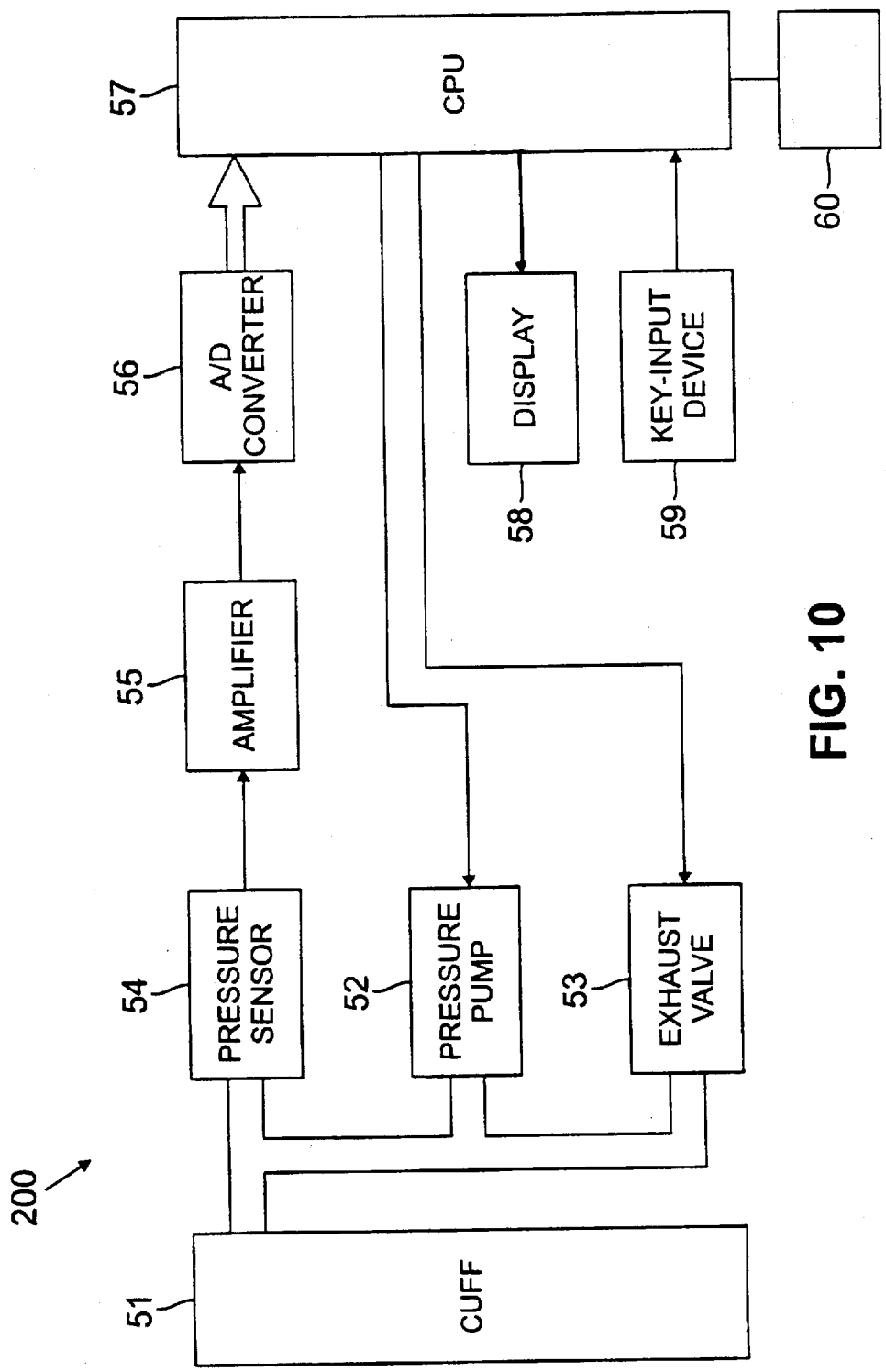
FIG. 10 is a block diagram of a device for estimating a degree of arteriosclerosis in a body.

Referring to FIG. 10, a device 200 for determining blood pressure and a degree of arteriosclerosis, like device 50, includes a cuff 51, a pressure pump 52, an exhaust valve 53 a pressure sensor 54, an amplifier 55, an A/D converter 56, and a CPU 57. In addition, device 200 includes a display 58, a key-input device 59, and a memory 60.

Device 200, like device 50, generates the PV curve for a person to whom cuff 51 is attached. However, unlike device 50, device 200 goes on to compare the PV curve to a set of PV curves stored in memory 60 and associated with varying degrees of arteriosclerosis. Based on this comparison, device 200 determines the degree of arteriosclerosis of the person to whom cuff 51 is attached, and displays this information on display 58.

The PV curves stored in memory 60, which are generated through empirical studies or other approaches, can be classified based on characteristics (i.e., age or gender) of the person to whom they correspond. In this event, the proper set of the PV curves for comparison with the PV curves for the person to whom cuff 51 is attached can be determined based on information supplied through key-input device 59.

Figure 11:
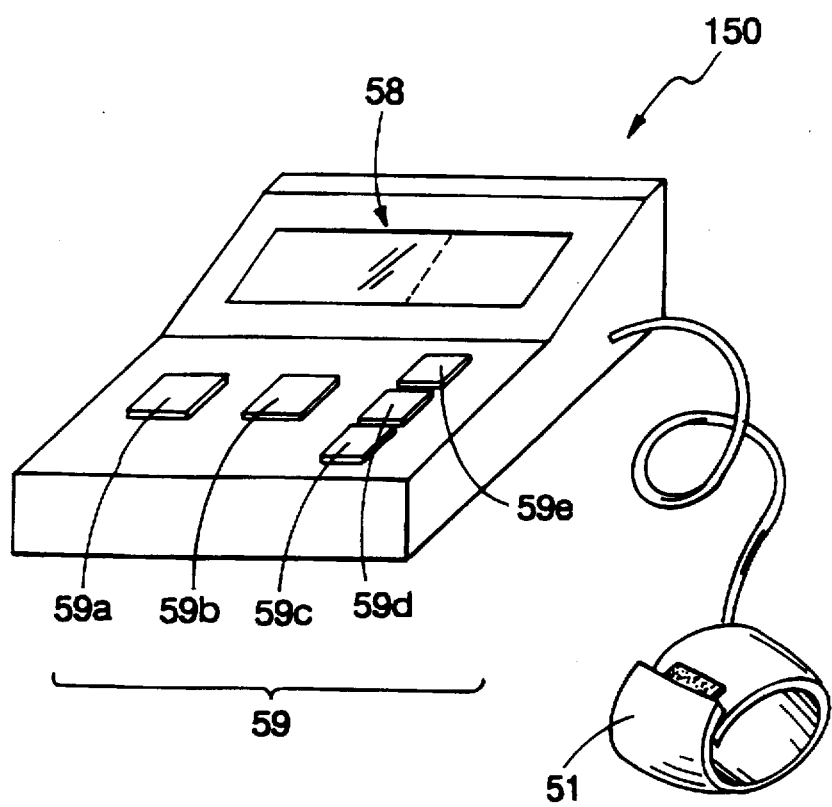
FIG. 11 is a perspective view of the device of FIG. 10.

As shown in FIG. 11, key-input device 59 includes keys 59a–59e. Where keys 59a and 59b are used, respectively, to turn device 200 on or off, while keys 59c–59e are used to supply information about the age of the person to whom cuff 51 is attached.

Figure 12:
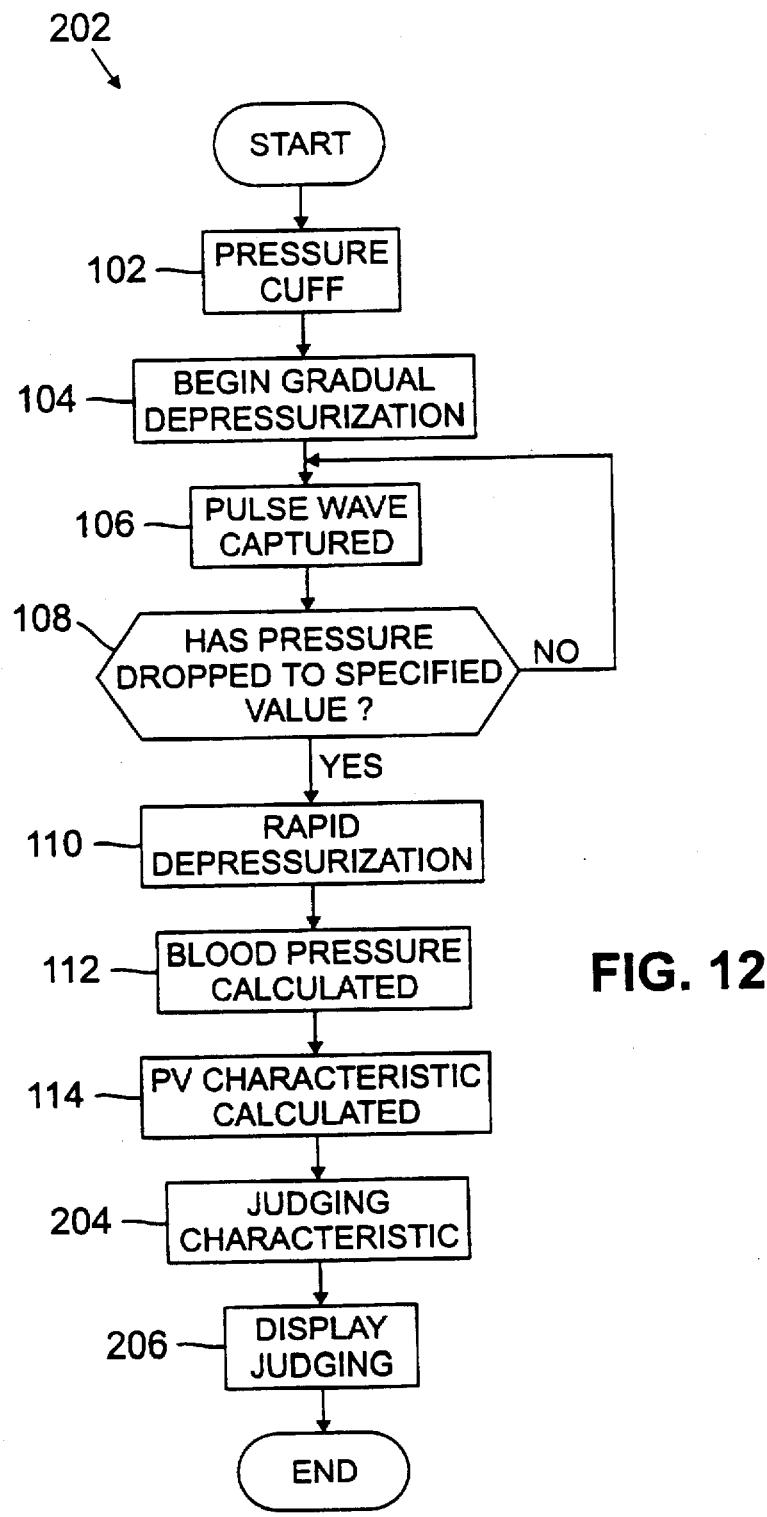
FIG. 12 is a flow chart of a procedure implemented by the device of FIG. 10.

As illustrated in FIG. 12, CPU 57 of device 200 implement a procedure 202 that is identical to procedure 100 implemented by the CPU 57 of device 50 with the exception that, after generating the PV curve (step 114), CPU 57 of device 200 judges the PV curve to determine a degree of arteriosclerosis by comparing the PV curve to the set of PV curves stored in memory 60 (step 204) and displays the results on display 58 (step 206).

Thus, with the invention, an artery in a person's arm or leg is pressurized by a cuff. The cuff pressure is detected during the process of pressurization or depressurization, the pulse wave component is extracted, and the pulse wave amplitude is detected. The systolic and diastolic pressures are obtained from cuff pressures and their corresponding pulse wave amplitudes. Next, a desired pulse wave and a pulse wave whose cuff pressure value is separated from the cuff pressure value corresponding to the desired pulse wave by one pulse pressure are chosen. The relationship between arterial pressure and internal volume is approximated by a function over the region of cuff pressures between those corresponding to the two chosen pulse waves. The pressure-to-volume curve is then calculated for a pressure value within the aforesaid region, and the process is repeated to obtain the pressure-to-volume curve for the region. Using this curve, the pressure-to-volume curve is determined for a range from full closure to full distension of the blood vessel. This curve is then compared to empirical data to determine a degree of arteriosclerosis. This method of measuring the pressure-to-volume curve, and determining the degree of arteriosclerosis, is non-invasive, non-surgical, simple, and highly accurate.

Other embodiments are within the following claims.

What is claimed is:

1. A measuring device for measuring a vascular function of an artery, comprising:
    a cuff that is attachable to a specified part of a body to constrict the artery;
    a pulse wave amplitude calculating device that calculates amplitudes of a series of pulse waves that are synchronous with successive systolic and diastolic pressures in said artery and are based on changes in volume of the artery between said systolic and diastolic pressures; and,
    an inference device that infers a vascular function that includes data indicating the degree of sclerosis of an artery and that corresponds to a pressure-to-volume characteristic of said artery based on said amplitudes of said series of pulse waves and corresponding cuff pressures in said cuff.

2. The measuring device of claim 1, wherein said inference device comprises a processor that:
    selects a first pulse wave,
    selects a second pulse wave having a corresponding cuff pressure that is separated from a cuff pressure corresponding to the first pulse wave by an amount equal to the difference between a systolic and diastolic blood pressure of the body to whom said cuff is attached, and
    approximates a function that corresponds to the relationship between the arterial pressure and the internal volume of the artery when the cuff pressure is in the region between the cuff pressures corresponding to the first and second pulse waves.

3. The measuring device of claim 2, wherein the processor uses the approximated function to determine the relationship between the arterial pressure and the internal volume of the artery when the cuff pressure is in a region between the cuff pressure corresponding to the second pulse wave and a cuff pressure corresponding to the second pulse wave plus the difference between a systolic and diastolic blood pressure of the body to whom the cuff is attached.

4. The measuring device of claim 3, wherein the processor interpolates data about the relationship between the arterial pressure and the internal volume of the artery to determine the relationship between the arterial pressure and the internal volume of the artery when the cuff pressure is greater than the cuff pressure corresponding to the second pulse wave plus the difference between the systolic and diastolic blood pressure of the body to whom the cuff is attached.

5. The measuring device of claim 3, wherein the approximated function is an exponential function of pressure.

6. The measuring device of claim 1, wherein the pulse wave amplitude calculating device comprises:
    a pulse wave extracting device that detects and extracts a pulse wave component that is synchronous with a heartbeat and is based on a change in a volume of an artery, and
    an amplitude calculating device that calculates an amplitude of the pulse wave.

7. The measuring device of claim 1, wherein said pulse wave amplitude calculating device calculates the amplitude of multiple pulse waves as a pressure in said cuff changes.

8. The measuring device of claim 1, further comprising:
    a pressure control device to change the cuff pressure within said cuff; and
    a cuff pressure detecting device to detect the cuff pressure within said cuff.

9. The measuring device of claim 1, wherein said pulse wave amplitude calculating device calculates the amplitude of multiple pulse waves as the pressure in said cuff decreases.

10. The measuring device of claim 9, wherein the pressure in said cuff decreases in step fashion.

11. The measuring device of claim 9, wherein the pressure in said cuff decreases steadily.

12. The measuring device of claim 1, wherein said pulse wave amplitude calculating device calculates the amplitude of multiple pulse waves as the pressure in said cuff increases.

13. The measuring device of claim 12, wherein the pressure in said cuff increases in step fashion.

14. The measuring device of claim 12, wherein the pressure in said cuff increases steadily.

15. A blood pressure meter, comprising:
    a cuff that is attachable to a specified part of a body to constrict an artery;
    a pulse wave extracting device to detect and extract a series of pulse waves that are synchronous with successive systolic and diastolic pressures and are based on changes in volume of said artery between said systolic and diastolic pressures;
    an amplitude calculating device to calculate amplitudes of said series of pulse waves;
    a blood pressure calculating device to calculate a systolic blood pressure and a diastolic blood pressure based on said cuff pressure and said amplitudes of said series of pulse waves;
    an inference device to infer a vascular function that includes data indicating the degree of sclerosis of an artery and that corresponds to a pressure-to-volume characteristic of said artery based on said amplitudes of said series of pulse waves and said corresponding cuff pressures in said cuff; and
    a judging device to determine a degree of sclerosis in said artery based on said vascular function.

16. The blood pressure meter of claim 15, wherein said judging device judges the degree of sclerosis in said artery by comparing said pressure-to-volume characteristic to a predetermined pressure-to-volume characteristic.

17. The blood pressure meter of claim 16, further comprising an input device to input an age of the body to whom said cuff is attached, wherein said judging device uses said age to select said predetermined pressure-to-volume characteristic.

18. The blood pressure meter of claim 15, further comprising a display to display said degree of sclerosis determined by said judging device.

19. A method of measuring vascular function of an artery, comprising:

attaching a cuff to a specified part of a body to constrict the artery;

calculating the amplitude of a pulse wave, the pulse wave being synchronous with a heartbeat and based on a change in volume of the artery; and inferring a vascular function that corresponds to a pressure-to-volume characteristic for the artery based on the amplitude of the pulse wave and a corresponding cuff pressure in the cuff.

* * * * *